United States Patent [19]

Harrison et al.

[11] 4,291,160

[45] Sep. 22, 1981

[54] 7-(1,3-DITHIOLAN-2-IMINO)-$\Delta^2$-CEPHALOSPORANIC ACID DERIVATIVES

[75] Inventors: Boyd L. Harrison; Joseph E. Dolfini, both of Cincinnati, Ohio

[73] Assignee: Richardson-Merrell Inc., Wilton, Conn.

[21] Appl. No.: 91,464

[22] Filed: Nov. 5, 1979

Related U.S. Application Data

[62] Division of Ser. No. 19,415, Mar. 12, 1979, Pat. No. 4,208,516.

[51] Int. Cl.$^3$ ............................................. C07D 501/16
[52] U.S. Cl. ........................................ 544/17; 544/27; 424/246

[58] Field of Search ...................... 544/17, 27, 26, 28, 544/30, 21

[56] References Cited

U.S. PATENT DOCUMENTS

| | | | |
|---|---|---|---|
| 3,821,198 | 6/1974 | Lee et al. | 260/245.2 |
| 4,034,090 | 7/1977 | Berger et al. | 424/246 |
| 4,088,761 | 5/1978 | Berger et al. | 424/246 |
| 4,119,778 | 10/1978 | Gordon | 424/246 |
| 4,169,946 | 10/1979 | Gordon | 424/246 |
| 4,172,941 | 10/1979 | Harrison et al. | 544/28 |

Primary Examiner—Nicholas S. Rizzo
Attorney, Agent, or Firm—William J. Stein

[57] ABSTRACT

Novel 7-(1,3-dithiolan-2-imino)-$\Delta^2$-cephalosporanic acid derivatives are described which possess useful antibacterial properties.

4 Claims, No Drawings

7-(1,3-DITHIOLAN-2-IMINO)-Δ²-CEPHALOSPORANIC ACID DERIVATIVES

This is a division of application Ser. No. 19,415, filed Mar. 12, 1979, now U.S. Pat. No. 4,208,516.

TECHNICAL FIELD

This invention relates to certain cephalosporin derivatives useful as antibacterial agents and to a method for their preparation.

BACKGROUND ART

Compounds with a cephalosporin nucleus belong to a well-known family of antibiotics that have been widely used in recent years for the treatment of various infectious diseases. A number of commercially useful cephalosporin antibiotics have been obtained by varying the substitution at the 3-position of the cephalosporin nucleus and by various modifications of the side-chain substituents at the 7-position of the cephalosporin nucleus. The search continues, however, for new compounds which possess a broad spectrum of antibacterial activity and which possess a high degree of activity toward both gram-positive and gram-negative bacteria without causing undesirable contraindications when administered to humans.

In an effort to improve upon the antibacterial properties of existing compounds, efforts have been directed towards the introduction of a 1,3-dithiolan ring directly at the 7-position of the cephalosporin nucleus. More particularly, the preparation of such cephalosporanic acid derivatives having in addition an acyl or alkyl derivative in the 4-position and a shift of unsaturation to the $\Delta^2$-position of the cephalosporin nucleus provides a novel class of cephalosporin derivatives that are effective against one or more gram-positive and gram-negative microorganisms. Accordingly, the compounds of the present invention are effective in the treatment of various infectious diseases caused by such gram-positive and gram-negative bacteria in poultry or in mammals including man. The compounds herein disclosed are suitable for use in certain topical germicidal preparations or as surface disinfectants.

SUMMARY OF THE INVENTION

In accordance with this invention certain novel 7-(1,3-dithiolan-2-imino)-$\Delta^2$-cephalosporanic derivatives are described, that are useful for their antibacterial properties. More particularly, this invention relates to certain 4-alkylated or 4-acylated derivatives of 7-(1,3-dithiolan-2-imino)-$\Delta^2$-cephalosporanic acids having the formula:

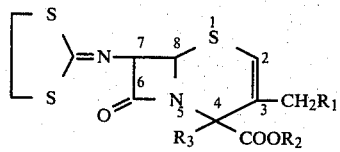

wherein $R_1$ is selected from the group consisting of hydrogen, acetoxy, 5-methyl-1,3,4-thiadiazol-2-ylthio, 1-methyl-1,2,3,4-tetrazol-5-ylthio and 1,2,3-triazol-4-ylthio; $R_2$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; $R_3$ is selected from the group consisting of alkyl having from 1 to 4 carbon atoms, carboxymethyl, alkoxycarbonyl and (alkoxycarbonyl)methyl wherein the alkoxy group has from 1 to 4 carbon atoms, halomethyl, benzyl and substituted benzyl wherein the benzyl substituent is methoxy or halo; and the pharmaceutically acceptable salts thereof.

Another aspect of this invention relates to the preparation of these novel 7-(1,3-dithiolan-2-imino)-$\Delta^2$-cephalosporanic acid derivatives by reacting a 7-(1,3-dithiolan-2-imino)cephalosporanic acid having the formula

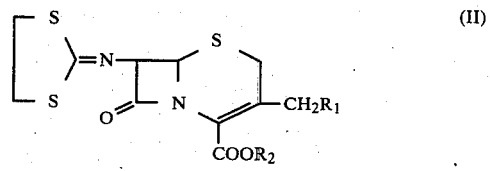

with an alkylating or acylating agent having the formula $R_3Y$, wherein the symbols $R_1$, $R_2$ and $R_3$ are as previously defined and Y is a leaving group selected from the group consisting of halogen, alkoxy, alkylthio, alkoxycarbonylthio, $-OSO_2Z$ and

wherein Z is alkyl, alkoxy and tolyl and each of the alkyl or alkoxy groups have from 1 to 4 carbon atoms; reacting said cephalosporanic acid and alkylating or acylating agent in an anhydrous organic solvent at a temperature of from $-78°$ C. to $30°$ C. for a period of from 1 to 24 hours in the presence of a strong base; and recovering the 7-(1,3-dithiolan-2-imino)-$\Delta^2$-cephalosporanic acid therefrom.

This process is particularly useful in that it provides a convenient method for the direct insertion of various alkyl, substituted alkyl or substituted acyl groups directly at the 4-position of the cephalosporin nucleus.

DETAILED DESCRIPTION OF THE INVENTION

As can be seen in formula (1) above, all of the compounds of this invention contain a 1,3-dithiolan-2-imino moiety attached directly to the 7-position of $\Delta^2$-cephalosporin nucleus. In addition, all of the compounds contain an alkyl, substituted alkyl or substituted acyl group at the 4-position of a $\Delta^2$-cephalosporin nucleus.

The term cephalosporanic acid derivatives as used herein relates in general to the specific cephalosporanic acids defined by the various substituents on the 3-methyl group of the cephalosporin nucleus. Thus, where the symbol $R_1$ is hydrogen, the compounds are designated as desacetoxycephalosporanic acids. When the symbol $R_1$ represents the acetoxy group, the compounds are specifically designated as belonging to the class of cephalosporanic acids. Finally, the symbol $R_1$ can represent a heterocyclic thioether attached to the 3-methyl group of the cephalosporin nucleus. The preferred heterocyclic thio-ethers described herein include the 5-methyl-1,3,4-thiadiazol-2-ylthio group, the 1-methyl-1,2,3,4-tetrazol-5-ylthio group and the 1,2,3-triazol-4-ylthio group. In order to be consistent with the nomenclature employed herein, these heterocyclic thio-ethers are designated as 3-[(heterocycle-ylthio)methyl]-decephalosporanic acids.

The compounds contemplated within the scope of this invention include not only the free cephalosporanic acids, but certain esters thereof as further indicated by the symbol $R_2$. Thus, where the symbol $R_2$ represents hydrogen, the free acid is designated. The preferred cephalosporanic acid ester groups include the t-butyl, 2,2,2-trichloroethyl, benzhydryl, formyloxymethyl and alkanoyloxymethyl groups. The term alkanoyl as used in this regard includes those groups having a total of from 2 to 5 carbon atoms, as for example, the acetyl, propionyl, butyryl, isobutyryl, 2-methylbutyryl, 3-methylbutyryl and 2,2-dimethylpropionyl groups. In general, these ester groups confer improved absorption properties upon the molecule, while remaining physiologically labile. Such esters are readily absorbed from the gastrointestinal tract, thereby promoting oral activity, whereupon they are enzymatically hydrolyzed to the corresponding free, and generally more active, cephalosporanic acids. These esters are readily prepared in accordance with the procedures described by Binderup et al., Journal of Antibiotics, 24, 767 (1971).

All of the compounds of this invention contain an alkyl, substituted alkyl or substituted acyl group at the 4-position of the cephalosporin nucleus as defined by the symbol $R_3$. When $R_3$ represents an alkyl group, a preferred sub-generic group of compounds is delineated. As employed herein, the term alkyl or alkoxy is intended to refer to those straight or branched chain groups having from 1 to 4 carbon atoms, e.g., methyl, methoxy, ethyl, ethoxy, propyl, propoxy, butyl, butoxy, isopropyl, isopropoxy, isobutyl, isobutoxy, sec. butyl and sec. butoxy.

The remaining alkyl groups defined by the symbol $R_3$ can be regarded as being substituted methyl derivatives. Thus, the symbol $R_3$ also represents a carboxy substituted methyl group, termed herein as the carboxymethyl group; a formic acid ester substituted methyl group, termed herein as an alkoxycarbonylmethyl group; a halogen substituted methyl group, designated herein as an halomethyl group; and a phenyl or (substituted)phenyl methyl group, designated herein as a benzyl or substituted benzyl group. The phenyl portion of the benzyl group may remain unsubstituted or can be mono-substituted in either of the ortho, meta or para positions of the phenyl ring with a halogen or a methoxy group. As used herein and throughout the specification, the term halogen is intended to particularly include the fluorine, chlorine and bromine members of the halogen family.

The symbol $R_3$ also includes certain acyl groups substituted at the 4-position of the cephalosporin nucleus. More particularly, various lower alkyl esters of formic acid are contemplated to be within the scope of this invention and are collectively designated as an alkoxycarbonyl group, wherein the term alkoxy is as previously defined.

The pharmaceutically acceptable salts of the compounds of formula (1) include the non-toxic, carboxylic acid salts that are formed with any suitable inorganic or organic base. Illustratively, these salts include those of alkali metals, as for example, sodium and potassium; alkaline earth metals, such as barium, calcium and magnesium; light metals of Group III A including aluminum; and organic primary, secondary and tertiary amines including triethylamine, procaine, dibenzylamine, vinylamine, N,N'-dibenzylethylenediamine, dihydroabietylamine, N-(lower)alkylpiperidine and various other amines that have been used to form non-toxic salts of antibiotics such as benzylpenicillin. These salts are prepared via conventional methods known to those skilled in the art, as for example by the neutralization of a solution of the free carboxylic acid in a polar solvent using a stoichiometric quantity of base, and recovering the salt therefrom.

Illustrative compounds encompassed by formula (1) above include:

7-(1,3-dithiolan-2-imino)-4-ethyl-$\Delta^2$-cephalosporanic acid, 7-(1,3-dithiolan-2-imino)-4-carboxymethyl-$\Delta^2$-cephalosporanic acid, t-butyl 7-(1,3-dithiolan-2-imino)-4-ethoxycarbonyl-$\Delta^2$-cephalosporanate, 2,2,2-trichloroethyl 7-(1,3-dithiolan-2-imino)-4-butoxycarbonyl-$\Delta^2$-cephalosporanate, benzhydryl 7-(1,3-dithiolan-2-imino)-4-methoxycarbonylmethyl-$\Delta^2$-cephalosporanate, formyloxymethyl 7-(1,3-dithiolan-2-imino)-4-chloromethyl-$\Delta^2$-cephalosporanate, pivaloyloxymethyl 7-(1,3-dithiolan-2-imino)-4-benzyl-$\Delta^2$-cephalosporanate, 7-(1,3-dithiolan-2-imino)-4-isopropyl-$\Delta^2$-desacetoxycephalosporanic acid, 7-(1,3-dithiolan-2-imino)-4-methoxycarbonyl-$\Delta^2$-desacetoxycephalosporanic acid, formyloxymethyl 7-(1,3-dithiolan-2-imino)-4-butyl-$\Delta^2$-desacetoxycephalosporanate, pivaloyloxymethyl 7-(1,3-dithiolan-2-imino)-4-carboxymethyl-$\Delta^2$-desacetoxycephalosporanate, benzhydryl 7-(1,3-dithiolan-2-imino)-4-bromomethyl-$\Delta^2$-desacetoxycephalosporanate, t-butyl 7-(1,3-dithiolan-2-imino)-4-p-methoxybenzyl-$\Delta^2$-desacetoxycephalosporanate, 7-(1,3-dithiolan-2-imino)-4-butyl-3-[(5-methyl-1,3,4-thiadiazol-2-ylthio)methyl]-$\Delta^2$-decephalosporanic acid, 7-(1,3-dithiolan-2-imino)-4-carboxymethyl-3-[(5-methyl-1,3,4-thiadiazol-2-ylthio)methyl]-$\Delta^2$-decephalosporanic acid, t-butyl 7-(1,3-dithiolan-2-imino)-4-butoxycarbonyl)-3-[(5-methyl-1,3,4-thiadiazol-2-ylthio)methyl]-$\Delta^2$-decephalosporanate, benzhydryl 7-(1,3-dithiolan-2-imino)-4-ethoxycarbonylmethyl-3-[(5-methyl-1,3,4-thiadiazol-2-ylthio)methyl]-$\Delta^2$-decephalosporanate, acetyloxymethyl 7-(1,3-dithiolan-2-imino)-4-benzyl-3-[(5-methyl-1,3,4-thiadiazol-2-ylthio)methyl]-$\Delta^2$-decephalosporanate, 2-methylbutyryloxymethyl 7-(1,3-dithiolan-2-imino)-4-o-bromobenzyl-3-[(5-methyl-1,3,4-thiadiazol-2-ylthio)methyl]-$\Delta^2$-decephalosporanate, 7-(1,3-dithiolan-2-imino)-4-methyl-3-[(1-methyl-1,2,3,4-tetrazol-5-ylthio)methyl]-$\Delta^2$-decephalosporanic acid, 7-(1,3-dithiolan-2-imino)-4-propoxycarbonyl-3-[(1-methyl-1,2,3,4-tetrazol-5-ylthio)methyl]-$\Delta^2$-decephalosporanic acid, t-butyl 7-(1,3-dithiolan-2-imino)-4-butoxycarbonylmethyl-3-[(1-methyl-1,2,3,4-tetrazol-5-ylthio)methyl]-$\Delta^2$-decephalosporanate, 2,2,2-trichloroethyl 7-(1,3-dithiolan-2-imino)-4-chloromethyl-3-[(1-methyl-1,2,3,4-tetrazol-5-ylthio)methyl]-$\Delta^2$-decephalosporanate, formyloxymethyl 7-(1,3-dithiolan-2-imino)-4-benzyl-3-[(1-methyl-1,2,3,4-tetrazol-5-ylthio)methyl]-$\Delta^2$-decephalosporanate, pivaloyloxymethyl 7-(1,3-dithiolan-2-imino)-4-m-methoxybenzyl-3-[(1-methyl-1,2,3,4-tetrazol-5-ylthio)methyl]-Δ²-decephalosporanate, 7-(1,3-dithiolan-2-imino)-4-carboxymethyl-3-[(1,2,3-triazol-4-ylthio)methyl]-Δ²-decephalosporanic acid, 7-(1,3-dithiolan-2-imino)-4-benzyl-3-[(1,2,3-triazol-4-ylthio)methyl]-Δ²-decephalosporanic acid, pivaloyloxymethyl 7-(1,3-dithiolan-2-imino)-4-chloromethyl-3-[(1,2,3-triazol-4-ylthio)methyl]-Δ²-decaphalosporanate.

formyloxymethyl 7-(1,3-dithiolan-2-imino)-4-ethoxycarbonyl-3-[(1,2,3-triazol-4-ylthio)methyl]-Δ²-decephalosporanate, 2,2,2-trichloroethyl 7-(1,3-dithiolan-2-imino)-p-chlorobenzyl-3-[(1,2,3-triazol-4-ylthio)methyl]-Δ²-decephalosporanate, and t-butyl 7-(1,3-dithiolan-2-imino)-o-methoxybenzyl-3-[(1,2,3-triazol-4-ylthio)methyl]-Δ²-decephalosporanate.

The 7-(1,3-dithiolan-2-imino)-Δ²-cephalosporanic acid derivatives of this invention are readily prepared by reacting a 7-(1,3-dithiolan-2-imino)cephalosporanic acid with an alkylating or acylating agent as indicated below.

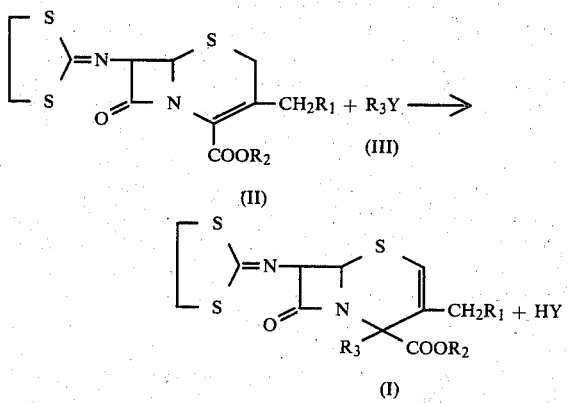

In the above reaction scheme the symbols $R_1$, $R_2$ and $R_3$ are as previously defined and the symbol Y represents a typical "leaving group". Thus, in the case where $R_3$ represents an alkyl or substituted alkyl group, the symbol Y can represent an anion such as halogen, alkoxy, alkylthio, alkoxycarbonylthio or $-OSO_2Z$, wherein the terms alkyl and alkoxy are as previously defined and Z is an alkyl, alkoxy or tolyl group. Where $R_3$ represents a carboxy or substituted acyl group, the symbol Y represents an anion such as

The reaction is conducted in the presence of a strong base, preferably an organometallic base of one of the alkali metals. These bases include the alkali lower alkoxides such as potassium t-butoxide, sodium methoxide, lithium methoxide, triphenylmethyl lithium, lithium alkylamides such as lithium diisopropylamide or lithium cyclohexyl isopropylamide, and alkali metal hydrides such as sodium and potassium hydride. Approximately one equivalent (or a slight excess thereof) is required for the strong base, calculated on the basis of the starting material. Preferably, the strong base of choice is a freshly prepared solution of lithium diisopropylamide.

The starting material, alkylating or acylating agent and the strong base are caused to react in an inert, anhydrous organic solvent which does not interfere with the reaction. Various inert solvents which can be employed include dimethoxyethane, dioxane, tetrahydrofuran, dimethylformamide, dimethylsulfoxide, benzene, ether and other related reaction media. The solvents most preferably employed include dimethylformamide or tetrahydrofuran and/or mixtures thereof.

The reaction is conducted at a temperature ranging from $-78°$ C. to $30°$ C. for a period of from 1 to 24 hours. Preferably the reaction is initially conducted at $-50°$ C. and gradually permitted to warm to room temperature with continued stirring. The reaction mixture is quenched by dilution and the desired product isolated using techniques well known to those skilled in the art. Thus, for example, the quenched reaction mixture is extracted with an organic solvent such as chloroform, methylene chloride or ether, the combined organic extracts are dried and evaporated in vacuo, and the residue is purified by crystallization from a suitable organic solvent or organic solvent mixture.

Depending upon the particular 7-(1,3-dithiolan-2-imino)cephalosporanic starting materials and reaction conditions employed, alkylation at the 4-position of the cephalosporin nucleus can result in the formation of both cis and trans isomers of the β-lactam nucleus. Thus, treatment of benzhydryl 7-(1,3-dithiolan-2-imino)desacetoxycephalosporanate or benzhydryl 7-(1,3-dithiolan-2-imino)cephalosporanate with lithium diisopropylamide in tetrahydrofuran at $-50°$ C., followed by addition of an alkylating agent such as methyl iodide and permitting the reaction mixture to warm to $20°$ C., affords good yields of benzhydryl 7-(1,3-dithiolan-2-imino)-4-methyl-Δ²-desacetoxycephalosporanate and 7-(1,3-dithiolan-2-imino)-4-methyl-Δ²-cephalosporanate, respectively, both with cis β-lactams. Treatment of t-butyl 7-(1,3-dithiolan-2-imino)desacetoxycephalosporanate under identical conditions affords a 1:1 mixture of the corresponding cis and trans β-lactam isomers.

On the other hand, treating benzhydryl 7-(1,3-dithiolan-2-imino)desacetoxycephalosporanate, benzhydryl 7-(1,3-dithiolan-2-imino)cephalosporanate, or t-butyl 7-(1,3-dithiolan-2-imino)desacetoxycephalosporanate with lithium diisopropylamide at $-50°$ C., permitting the reaction mixture to warm to $20°$ C. and then adding the alkylating agent at this elevated temperature, results in the formation of the corresponding 4-alkylated compounds having only the trans β-lactam configuration. Moreover, treatment of the 4-alkylated compounds having the cis β-lactam configuration with lithium diisopropylamide at temperatures above $20°$ C. can result in an epimerization at the 7-position to yield compounds having the trans β-lactam configuration. Thus, for example, a thermodynamic ratio of the trans:cis β-lactam isomers is achieved with benzhydryl 7-(1,3-dithiolan-2-imino)-4-methyl-Δ²-desacetoxycephalosporanate by treating this compound with triethylamine in dimethylsulfoxide at room temperature to $45°$ C. for approximately 90 hours.

The 7-(1,3-dithiolan-2-imino)cephalosporanic acids (II) used as starting materials are conveniently prepared and in good yield by condensing an S-alkylated salt of 1,3-dithiolane-2-thione (III) with a 7-aminocephalosporanic acid. This reaction sequence is indicated as follows wherein the symbols $R_1$ and $R_2$ are as previously defined and the symbol X represents a halogen atom selected from the group consisting of chlorine, bromine and iodine.

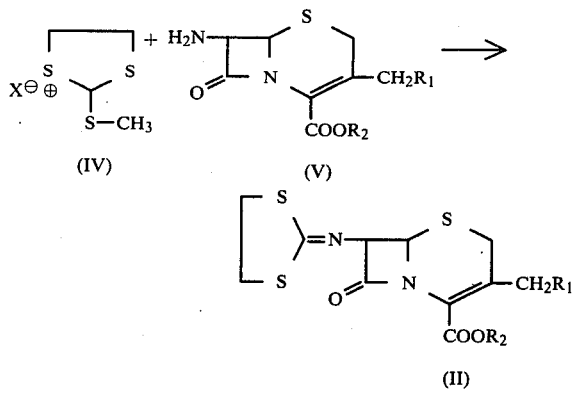

The S-alkylated salts of 1,3-dithiolane-2-thione are readily prepared by the alkylation of 1,3-dithiolane-2-thione, which is known commercially as ethylenetrithiocarbonate. Thus, for example, the addition of a methyl halide with stirring to a solution of 1,3-dithiolane-2-thione at a temperature ranging from 0° to about 50° C. for a period of from 1 to 24 hours results in the formation of the corresponding S-methyl halide salt of 1,3-dithiolene-2-thione as a crystalline salt. The S-methyl iodide salt of 1,3-dithiolane-2-thione is the alkylated salt of choice and is prepared by the addition of methyl iodide to a solution of 1,3-dithiolane-2-thione. Preferably, the reaction is conducted via the dropwise addition of methyl iodide to a nitromethane solution of 1,3-dithiolane-2-thione at room temperature under an inert atmosphere such as nitrogen or argon.

The various 7-aminocephalosporanic acids employed herein (V) are well-known compounds previously described in the literature. Thus, hydrolysis of cephalosporin C results in the formation of 7-aminocephalosporanic acid as described by Loder et al., Biochem. J. 79, 408–16 (1961) and represented by the formula

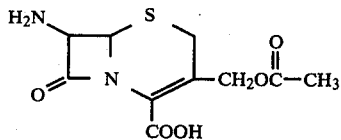

The compound 7-aminodesacetoxycephalosporanic acid, having the formula

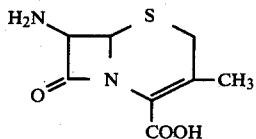

is prepared by the catalytic reduction of cephalosporin C, followed by the hydrolytic removal of the 5-aminoadipoyl side chain as described in U.S. Pat. No. 3,129,224.

The 7-aminocephalosporanic acid derivatives (V) are readily condensed as their free acids to form the 7-(1,3-dithiolan-2-imino)cephalosporanic acid derivatives (II) used as starting materials. Preferably, however, they are condensed in the form of their salts or their esters. Suitable salts include the sodium and trialkylamine salts, in which the alkyl group contains from 1 to 5 carbon atoms. Suitable esters include any of the esters disclosed in U.S. Pat. No. 3,284,451, or any of the silyl esters analogously disclosed in U.S. Pat. No. 3,249,622. The condensed esters are readily isolated or, as in the case of the silyl esters, they are readily cleaved to yield the free acids of the various 7-(1,3-dithiolan-2-imino) cephalosporanic acid derivatives.

In general, the condensation of the 7-aminocephalosporanic acid derivatives (V) and the S-alkylated salts of 1,3-dithiolan-2-thione (IV) is conducted in the presence of a suitable solvent at temperatures ranging from −30° C. to 100° C. The reaction time varies from 15 minutes to as long as 36 hours depending upon the particular reaction temperature employed. For convenience, the reaction is preferably conducted at room temperature or slightly below for a period of from 1 to 8 hours.

Suitable solvents in which the condensation takes place include acetone, acetonitrile, dioxane, dimethylformamide, chloroform, ethylene chloride, dichloromethane and tetrahydrofuran with acetonitrile being the particular solvent of choice. In certain instances, as when the 7-aminocephalosporanic acid starting materials are present in the form of a salt, mixtures of water and a miscible organic solvent may be advantageously employed. Optionally, the condensation can be conducted in the presence of an inert atmosphere, as for example argon or nitrogen gas. An excess of the S-alkylated salt of 1,3-dithiolane-2-thione (IV) is also favorably employed to insure completeness of the reaction and to favor the yield of desired product obtained.

Following completion of the condensation reaction, the reaction mixture is generally quenched in water and the desired 7-(1,3-dithiolan-2-imino)cephalosporanic acid derivatives isolated via standard procedures known to those versed in the art. Thus, for example, the quenched reaction mixture is extracted with a suitable organic solvent, such as chloroform, methylene chloride or ether, the organic extract is washed with a dilute aqueous acid solution to remove any unreacted starting material, the washed organic extract is dried, concentrated and the desired 7-(1,3-dithiolan-2-imino)cephalosporanic acid derivatives recovered therefrom. Purification of the products is generally effected by recrystallization from suitable organic solvents such as chloroform from a chloroform-ether mixture.

When the 7-aminocephalosporanic acid derivatives (V) are present as the free acid, i.e., where the symbol $R_2$ is hydrogen, the use of a silylating agent is advantageously employed. Under these circumstances the condensation best proceeds under anhydrous conditions in anhydrous solvents in which the free acids are not too soluble. The silylating agents employed form labile silyl esters with the various 7-aminocephalosporanic acids and are readily soluble in anhydrous solvents. Inasmuch as these silyl esters are highly sensitive to moisture, once condensation has taken place, the esters are readily hydrolyzed to the free acid by quenching the reaction mixture in water. Suitable silylating agents that may be favorably employed include various alkyl chlorosilanes, alkyl disilazanes, alkyl silylamines and alkylsilylamides, as for example triethyl chlorosilane, tri-n-butyl chlorosilazane, dimethylethyl chlorosilane, phenylethylmethyl chlorosilane, triphenyl chlorosilane, tetraethyldimethyl disilazane, hexamethyl disilazane, tetramethyldiphenyl disilazane, hexaphenyl disilazane, N-ethyl triethyl silylamine, triphenyl silylamine, N-trimethylsilylacetamide with the silylating agent of choice being O,N-bis-trimethylsilylacetamide.

In general, the free acids of the 7-aminocephalosporanic acid derivatives (V), are suspended in a suitable anhydrous solvent, as for example acetonitrile, tetrahydrofuran or dioxane. Two equivalents of the silylating agent are added to this suspension and stirring is continued until esterification and solution occur, generally in about two hours or less at room temperature. An additional 10% excess of the silylating agent is added to insure complete esterification of the particular 7-aminocephalosporanic acid employed. Condensation with an S-alkylated salt of 1,3-dithiolane-2-thione and the subsequent isolation of the desired products remain essentially as previously described.

A preferred group of 7-(1,3-dithiolan-2-imino)-4-substituted-$\Delta^2$-cephalosporanic acid derivatives (I) are those containing a methylthioheterocycle group at the 3-position of the cephalosporin nucleus. In addition to the condensation procedure described above, these compounds can be prepared by a displacement of the 3-acetoxy group of a salt or ester of a 7-(1,3-dithiolan-2-imino)-4-substituted-$\Delta^2$-cephalosporanic acid. This displacement or solvolysis of the acetoxy group at the 3-methyl position of the cephalosporin nucleus is a well-known reaction described in U.S. Pat. Nos. 3,516,997 and 3,641,021. The acetoxy group is readily displaced with a heterocyclic thiol, such as 5-methyl-1,3,4-thiadiazol-2-ylthio, 1-methyl-1,2,3,4-tetrazol-5-ylthio or 1,2,3-triazol-4-thiol at temperatures ranging from about 25° C. to 150° C. in aqueous solvents such as water or buffered aqueous solutions. Preferably, a temperature range of from 50° C. to 100° C. is employed in combination with a buffered aqueous solution having a pH ranging from 4.0 to 9.0. Suitable aqueous solutions include those selected from the group consisting of water, or an aqueous solution of acetone, tetrahydrofuran and dimethylformamide.

The novel compounds of the present invention are useful antimicrobial agents having a broad spectrum of antimicrobial activity in vitro against standard laboratory microorganisms that are routinely used to demonstrate activity against pathogenic bacteria. The antibacterial spectrum of typical compounds described herein is determined in a standard manner by means of a qualitative diffusion assay as illustrated in Example 7 below. The in vitro antibacterial activity of the novel compounds of this invention not only makes them useful as pharmacological agents per se, but makes them useful as additives for animal feeds, as well as additives for materials which are subject to microbial deterioriation, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

Benzhydryl 7-(1,3-dithiolan-2-imino)-4-methyl-$\Delta^2$-cephalosporanate

Butyl lithium, 0.46 ml, is added with stirring to 0.16 ml of diisopropylamine dissolved in 10 ml of dry tetrahydrofuran (freshly distilled from lithium aluminum anhydride) at −50° C. under an argon blanket. A solution of 0.54 g of benzhydryl 7-(1,3-dithiolan-2-imino)-cephalosporanate dissolved in 10 ml of dimethylformamide is added with stirring to the prepared lithium diisopropylamide solution at −50° C. To the red-colored solution that forms is added 0.8 ml of methyl iodide. The reaction mixture is stirred at −50° C. for 10 minutes and allowed to warm to room temperature with continued stirring for an additional 20 minutes. The reaction mixture is quenched in pH 4.5 phosphate buffer, and the entire mixture extracted with chloroform. The chloroform extracts are combined, washed with water, dried (magnesium sulfate) and evaporated in vacuo to provide 0.68 g of a light yellow oil. This residue is purified by dissolving in an ether/ethyl acetate mixture and extracting the solution three times with water and once with a saturated solution of sodium chloride. The organic layer is dried over anhydrous magnesium sulfate and the solvents are removed by evaporation in vacuo. The benzhydryl 7-(1,3-dithiolan-2-imino)-4-methyl-$\Delta^2$-cephalosporanate so obtained has the appearance of a solid light yellow dried foam and has a m.pt. of 55°–63° C. (dec.).

Following essentially the same procedure, but substituting t-butyl 7-(1,3-dithiolan-2-imino)cephalosporanate, 2,2,2-trichloroethyl 7-(1,3-dithiolan-2-imino)cephalosporanate, formyloxymethyl 7-(1,3-dithiolan-2-imino)cephalosporanate and pivaloyloxymethyl 7-(1,3-dithiolan-2-imino)cephalosporanate for the benzhydryl 7-(1,3-dithiolan-2-imino)cephalosporanate above, results in the formation of t-butyl 7-(1,3-dithiolan-2-imino)-4-methyl-$\Delta^2$-cephalosporanate, 2,2,2-trichloroethyl 7-(1,3-dithiolan-2-imino)-4-methyl-$\Delta^2$-cephalosporanate, formyloxymethyl 7-(1,3-dithiolan-2-imino)-4-methyl-$\Delta^2$-cephalosporanate and pivaloyloxymethyl 7-(1,3-dithiolan-2-imino)-4-methyl-$\Delta^2$-cephalosporanate, respectively.

EXAMPLE 2

Benzhydryl 7-(1,3-dithiolan-2-imino)-4-methyl-$\Delta^2$-desacetoxycephalosporanate To a solution of 0.82 ml of diisopropylamine dissolved in 50 ml of dry tetrahydrofuran (freshly distilled from lithium aluminum hydride) is added 2.3 ml of butyl lithium with stirring at −50° C. under a blanket of argon. A solution of 2.4 g of benzhydryl 7-(1,3-dithiolan-2-imino)desacetoxycephalosporanate dissolved in 20 ml of dry dimethylformamide is added via dropwise addition with stirring at −50° C. to this lithium diisopropylamide solution. The resulting light yellow solution is stirred at −50° C. for 20 minutes and a solution of 4.0 ml of methyl iodide dissolved in 10 ml of dimethylformamide is rapidly added thereto. To reaction mixture is stirred at −50° C. for 15 minutes and allowed to warm gradually to room temperature with continued stirring. The reaction mixture is quenched in pH 4.5 phosphate buffer and the whole extracted with chloroform. The chloroform extracts are combined, washed with water (three times), dried over anhydrous magnesium sulfate, and evaporated to dryness in vacuo. The light yellow oil is dissolved in ethyl acetate, diluted with ether and the resulting solution washed with water (three times), followed by a wash with a saturated solution of sodium chloride, and dried over anhydrous magnesium sulfate. Removal of the solvents in vacuo leaves the desired product, benzhydryl 7-(1,3-dithiolan-2-imino)-4-methyl-$\Delta^2$-desacetoxycephalosporanate as a solid yellow foam having a m.pt. of 65°–70° C. (dec.).

Following essentially the same procedure, but substituting benzhydryl 7-(1,3-dithiolan-2-imino)-3-[(5-methyl-1,3,4-thiadiazol-2-ylthio)methyl]decephalosporanate, benzhydryl 7-(1,3-dithiolan-2-imino)-3-[(1-methyl-1,2,3-tetrazol-5-ylthio)methyl]decephalosporanate and benzhydryl 7-(1,3-dithiolan-2-imino)-3-[(1,2,3-triazol-4-ylthio)methyl]decephalosporanate for the benzhydryl 7-(1,3-dithiolan-2-imino)desacetoxycephalosporanate above results in the formation of benzhydryl 7-(1,3-dithiolan-2-imino)-4-methyl-$\Delta^2$-3-[(5-methyl-1,3,4-thiadiazol-2-ylthio)methyl]decephalosporanate, benzhydryl 7-(1,3-dithiolan-2-imino)-4-methyl-$\Delta^2$-3-[(1-methyl-1,2,3-tetrazol-5-ylthio)methyl]decephalosporanate, and benzhydryl 7-(1,3-dithiolan-2-imino)-4-methyl-$\Delta^2$-3-[(1,2,3-triazol-4-ylthio)methyl]decephalosporanate, respectively.

EXAMPLE 3

Benzhydryl 7-(1,3-dithiolan-2-imino)-4-t-butoxycarbonylmethyl-$\Delta^2$-desacetoxycephalosporanate Butyl lithium, 0.23 ml, is added with stirring to 0.56 ml of diisopropylamine dissolved in 10 ml of dry tetrahydrofuran (freshly distilled from lithium aluminum hydride) at $-50°$ C. under an argon blanket. A solution of 0.24 g of the benzhydryl ester of 7-(1,3-dithiolan-2-imino)desacetoxycephalosporanic acid is dissolved in 5 ml of dry dimethylformamide and added at $-50°$ C. to the lithium diisopropylamide solution with stirring. Following continuous stirring for an additional 15 minutes, a solution of 0.12 ml of t-butyl bromoacetate dissolved in 1 ml of dimethylformamide is added via dropwise addition with stirring. The reaction mixture is allowed to warm slowly to room temperature with continuous stirring and is quenched in pH 4.5 phosphate buffer. The entire mixture is extracted with chloroform, the chloroform extracts combined, washed three times with water, dried over anhydrous magnesium sulfate, and evaporated to dryness in vacuo to a light orange oil. This oil is dissolved in a small amount of chloroform, applied to a previously prepared thin layer chromatography silica gel plate and a broad band collected having a Rf of 0.2–0.5. This band of material is dissolved in chloroform, filtered, and evaporated in vacuo to yield 0.22 g of benzhydryl 7-(1,3-dithiolan-2-imino)-4-t-butoxycarbonylmethyl-$\Delta^2$-desacetoxycephalosporanate, as a solid yellow foam having the following NMR characteristics:

NMR (CDCl$_3$) $\delta$1.43 (s, 9H), 1.77 (s, 3H), 3.40–3.75 (m, 6H), 4.83 (d, 1H, J=5 Hz), 5.53 (d, 1H, J=5 Hz), 6.13 (br.s, 1H), 6.93 (s, 1H), 7.40 (s, 10H).

Following essentially the same procedure, but substituting bromoacetic acid, chloromethyl mesylate, benzyl chloride and diethylcarbonate for the t-butyl bromoacetate above, results in the formation of benzhydryl 7-(1,3-dithiolan-2-imino)-4-carboxymethyl-$\Delta^2$-desacetoxycephalosporanate, benzhydryl 7-(1,3-dithiolan-2-imino)-4-chloromethyl-$\Delta^2$-desacetoxycephalosporanate, benzhydryl 7-(1,3-dithiolan-2-imino)-4-benzyl-$\Delta^2$-desacetoxycephalosporanate, and benzhydryl 7-(1,3-dithiolan-2-imino)-4-ethoxycarbonyl-$\Delta^2$-desacetoxycephalosporanate.

EXAMPLE 4

7-(1,3-Dithiolan-2-imino)-4-methyl-$\Delta^2$-desacetoxycephalosporanic acid

Benzhydryl 7-(1,3-dithiolan-2-imino)-4-methyl-$\Delta^2$-desacetoxycephalosporanate, 0.50 g, prepared in accordance with Example 2, is dissolved in 5 ml of reagent anisole and cooled to 0° C. Trifluoroacetic acid, 25 ml, is cooled to 5° C., added to the anisole solution and the reaction mixture is stirred for 30 minutes. The reaction mixture is poured into 150 ml of chloroform and evaporated in vacuo to near dryness. The residue is dissolved in diethyl ether and extracted with 50 ml portions of a 4% aqueous solution of sodium bicarbonate until the aqueous extracts remain basic. The sodium bicarbonate extracts are combined, 100 ml of chloroform added thereto and acidified to pH 2.5 with stirring. The aqueous solution is separated and extracted twice again with fresh chloroform. form. The combined chloroform extracts are combined, dried over anhydrous magnesium sulfate and evaporated to a dry white foam in vacuo. The foam is triturated with diethyl ether, filtered and dried to yield 7-(1,3-dithiolan-2-imino)-4-methyl-$\Delta^2$-desacetoxycephalosporanic acid having a m.pt. of 201°–3° C. (dec.).

Following essentially the same procedure, but substituting benzhydryl 7-(1,3-dithiolan-2-imino)-4-methyl-3-[(5-methyl-1,3,4-thiadiazol-2-ylthio)methyl]-$\Delta^2$-decephalosporanate, benzhydryl 7-(1,3-dithiolan-2-imino)-4-methyl-3-[(1-methyl-1,2,3-tetrazol-5-ylthio)methyl]-$\Delta^2$-decephalosporanate and benzhydryl 7-(1,3-dithiolan-2-imino)-4-methyl-3-[(1,2,3-triazol-4-ylthio)methyl]-$\Delta^2$-decephalosporanate for the benzhydryl 7-(1,3-dithiolan-2-imino)-4-methyl-$\Delta^2$-desacetoxycephalosporanate above results in the formation of 7-(1,3-dithiolan-2-imino)-4-methyl-3-[(5-methyl-1,3,4-thiadiazol-2-ylthio)-methyl]-$\Delta^2$-decephalosporanic acid, 7-(1,3-dithiolan-2-imino)-4-methyl-3-](1-methyl-1,2,3-tetrazol-5-ylthio)-methyl]-$\Delta^2$-decephalosporanic acid and 7-(1,3-dithiolan-2-imino)-4-methyl 3-](1,2,3-triazol-4-ylthio)methyl]-$\Delta^2$-decephalosporanic acid, respectively.

EXAMPLE 5

The following example illustrates the in vitro activity of the compounds described herein.

Trypticase soy broth is inoculated from a slant culture of the test bacterium the day prior to testing. The inoculated broth is incubated for 24 hours at 37° C. and 0.05 ml of the inoculated and incubated broth is added to 25 ml of melted (45°–50° C.) trypticase soy agar. The seeded agar is poured into a 100 mm square petri dish and allowed to solidify.

Approximately 1 to 3 mg of purified 7-(1,3-dithiolan-2-imino)-4-methyl-$\Delta^2$-desacetoxycephalosporanic acid is placed directly upon the agar and the agar plate is incubated overnight. The following day the agar plates are examined for clear zones of bacterial growth inhibition and the diameter of each zone measured and recorded. Using the test organism *Salmonella schottmuelleri,* a clear zone of bacterial inhibition measuring 2 mm in diameter is obtained, whereas with the test organism *Pseudomonas aeruginosa,* a clear zone of bacterial inhibition measuring 5 mm in diameter is obtained.

We claim:

1. A 7-(1,3-dithiolan-2-imino)-$\Delta^2$-cephalosporanic acid derivative having the formula

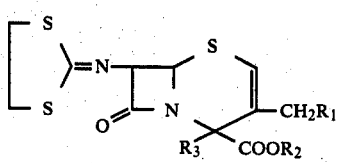

wherein
- $R_1$ is selected from the group consisting of 5-methyl-1,3,4-thiadiazol-2-ylthio, 1-methyl-1,2,3,4-tetrazol-5-ylthio and 1,2,3-triazol-4-ylthio;
- $R_2$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms;
- $R_3$ is selected from the group consisting of alkyl having from 1 to 4 carbon atoms, carboxymethyl, alkoxycarbonyl and (alkoxycarbonyl)methyl wherein the alkoxy group has from 1 to 4 carbon atoms, halomethyl, benzyl and substituted benzyl wherein the benzyl substituent is methoxy or halo;

and the pharmaceutically acceptable salts thereof.

2. A compound according to claim 1 wherein $R_3$ is alkyl.

3. A compound according to claim 1 wherein $R_3$ is (alkoxycarbonyl)methyl.

4. A process for the preparation of a compound of claim 1 which comprises reacting a 7-(1,3-dithiolan-2-imino)cephalosporanic acid having the formula

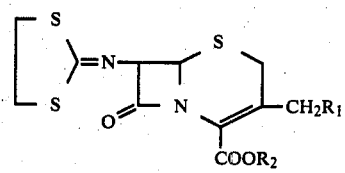

with an alkylating or acylating agent having the formula $R_3Y$ in which $R_1$ is selected from the group consisting of 5-methyl-1,3,4-thiadiazol-2-ylthio, 1-methyl-1,2,3,4-tetrazol-5-ylthio and 1,2,3-triazol-4-ylthio; $R_2$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; $R_3$ is selected from the group consisting of alkyl having from 1 to 4 carbon atoms, carboxymethyl, alkoxycarbonyl and (alkoxycarbonyl)methyl wherein the alkoxy group has from 1 to 4 carbon atoms, halomethyl, benzyl and substituted benzyl wherein the benzyl substituent is methoxy or halo; and Y is a leaving group selected from the group consisting of halogen, alkoxy, alkylthio, alkoxycarbonylthio, $-OSO_2Z$ and

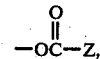

wherein Z is alkyl, alkoxy and tolyl and each of the alkyl or alkoxy groups have from 1 to 4 carbon atoms; reacting said cephalosporanic acid and alkylating or acylating agent in an anhydrous organic solvent at a temperature of from $-78°$ to $30°$ C. for a period of from 1 to 24 hours in the presence of a strong base; and recovering the 7-(1,3-dithiolan-2-imino)-$\Delta^2$-cephalosporanic acid therefrom.

* * * * *